US006767872B2

(12) United States Patent
Williams

(10) Patent No.: US 6,767,872 B2
(45) Date of Patent: Jul. 27, 2004

(54) ELASTOHYDRODYNAMIC AND BOUNDARY LUBRICANT AND METHOD OF LUBRICATING

(75) Inventor: John R. Williams, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 12 days.

(21) Appl. No.: 10/142,479

(22) Filed: May 10, 2002

(65) Prior Publication Data

US 2003/0087771 A1 May 8, 2003

Related U.S. Application Data

(60) Provisional application No. 60/337,765, filed on Dec. 2, 2001, and provisional application No. 60/291,882, filed on May 18, 2001.

(51) Int. Cl.$^7$ .......................................... C10M 131/00
(52) U.S. Cl. ...................... 508/421; 508/443; 508/504; 508/545; 508/551; 508/564; 508/570; 508/571; 508/577; 508/588
(58) Field of Search ................................ 508/501, 504, 508/551, 553, 421

(56) References Cited

U.S. PATENT DOCUMENTS

| | | | |
|---|---|---|---|
| 2,508,334 A | 5/1950 | Moyle | 260/479 |
| 3,798,265 A | 3/1974 | Bartlett | 260/534 |
| 3,804,885 A | 4/1974 | Reineke et al. | 260/487 |
| 3,931,325 A | 1/1976 | Doorenbos et al. | 260/586 R |
| 3,996,200 A | 12/1976 | Doorenbos et al. | 260/63 HA |
| 4,263,157 A | 4/1981 | Steiner et al. | 252/54.6 |
| 4,342,877 A | 8/1982 | Cheng et al. | 560/130 |
| 4,572,805 A | 2/1986 | Kaieda et al. | 260/465 D |
| 4,719,052 A | 1/1988 | Ohsaka et al. | 260/544 F |
| 4,757,145 A | 7/1988 | Caporiccio et al. | 546/81 |
| 4,835,304 A | 5/1989 | Williams | 560/144 |
| 4,941,987 A | 7/1990 | Strepparola et al. | 252/58 |
| 4,985,588 A | 1/1991 | Kumai et al. | 560/103 |
| 5,177,252 A | 1/1993 | Williams | 560/145 |
| 5,223,342 A | 6/1993 | Shoji et al. | 428/413 |
| 5,248,432 A | 9/1993 | Williams | 252/51.5 R |
| 5,382,614 A | 1/1995 | Scarati et al. | 524/108 |
| 5,435,927 A * | 7/1995 | Beckwith et al. | |
| 6,187,954 B1 * | 2/2001 | Falcone | 564/136 |
| 6,531,431 B2 * | 3/2003 | Mohri et al. | 508/551 |

FOREIGN PATENT DOCUMENTS

| | | |
|---|---|---|
| EP | 73539 | 3/1983 |
| EP | 89820 | 9/1983 |
| EP | 0 475393 A2 | 3/1992 |

OTHER PUBLICATIONS

Chem Abstract, vol. 101, 1984, 101:191,244u, Perfluoro and polyfluorosulfonic acids. XIII. Preparation and nucleophilic reaction of perfluorophenyl perfluoroalkanoates and perfluorophenoxycarbonyldifluoro–methanesulfonates, Chen.

Chem Abstract, vol. 92, 1980, 92:113332c Attenuator Dispersion. Lochner, Kaspar Ger. Offen. 2,814,366 (Cl. C10M 7/04), Oct. 18, 1979.

Chem Abstract, vol. 87, 1977, 87:137943a Medium for Damping Mechanical and Acoustical Vibrations. Lochner, Kaspar Ger. Offen. 2,549,672 (Cl. C10M3/20), May 12, 1977.

Chem Abstract, vol. 79, 1973, 81397r Use of Copolymers as Power Transfer and/or Damping Liquids or as Constituent of These Liquids. Secker, Fredericks J. S. (Shell Internationale Research Maatschappeij N.V.) Ger. No. 1,644,951 (Cl. C 10m) Jun. 7, 1973.

Customer Search Results, CAS Search Service, The American Chemical Society, (Reg. File Search Results P116412T), 8 substances 1957–date, Apr. 26, 1989, pp. 1–19.

De Pasquale, R. J., et al., NASA, Report No. N83–10195 (Aug. 1965).

Du Pont Manufactures Brochure on Krytox Fluorinated Oils (Aug. 1986).

Journal of Chromatography, vol. 284, pp. 157–165 (1984), Sha Shang–Zhi et al., QD 241J5.

Koehler, K. E., Charles Stark Draper Laboratory, Report No. C–5413 (Jun. 1981).

Lagow, R. J., Defense Technical Information Center Document, Report No. AFOSR–TR 82–1037 (1982).

Paciorek, K. J. L. et al, Copolymerization Studies of Fluorinated Epoxides, Ind. Eng. Chem. Prod. Res. Dev., 22, 5–8 (1983).

Persico, D. F., et al., Synthesis of Perfluoropolyethers via Hydrocarbon Polyesters: A New General Method, J. Am. Chem. Soc., 107, 1197–1201 (1985).

Soloski, E. J. and Tamborski, C., Synthesis of Perfluoro(polyether) Difunctional Compounds, J. Fluorine Chem. 11, 601–612 (1978).

Communication Relating to the Results of the Partial International Search for International Application No. PCT/US 02/14794 (2 pages).

* cited by examiner

*Primary Examiner*—Ellen M. McAvoy
(74) *Attorney, Agent, or Firm*—Testa, Hurwitz & Thibeault, LLP

(57) ABSTRACT

A lubricant compound for use for both boundary and elastohydrodynamic lubrication utilize a hydrocarbon boundary lubricant linked to one or more fluorocarbon elastohydrodynamic lubricants and may be employed alone or as an additive. The lubricant compound lubricates surfaces on which it is disposed over a range of conditions. The boundary lubricant and the elastohydrodynamic lubricant are substituted such that they react with and/or provide desirable lubrication properties for particular surfaces.

40 Claims, No Drawings

ELASTOHYDRODYNAMIC AND BOUNDARY LUBRICANT AND METHOD OF LUBRICATING

RELATED APPLICATIONS

This application claims the benefits of and priority to provisional patent application Serial No. 60/291,882 filed in the United States Patent Office on May 18, 2001 and provisional patent application Serial No. 60/337,765 filed in the United States Patent Office on Dec. 3, 2001, the entire contents of which are incorporated by reference herein.

FIELD OF THE INVENTION

The present invention relates to lubricants and lubricant additives.

BACKGROUND OF THE INVENTION

A lubricant is a substance capable of reducing friction, heat, and wear when introduced as a film between solid surfaces. Generally, lubrication is provided between solid surfaces to prevent contact between the surfaces, thereby reducing friction, wear, or both. The type of lubrication required for a particular application depends on a variety of factors, including the degree of motion between the surfaces.

Boundary lubricants are employed to physically or chemically treat surfaces in solid-to-solid surface contact that are at rest or at low relative speeds with respect to one another. Boundary lubricants generally undergo a controlled chemical reaction or physical interaction with one or both contact surfaces to form protective stationary films that discourage contact (and, hence, wear) therebetween.

Elastohydrodynamic lubrication, by contrast, lubricates surfaces that are in motion at high relative velocities. For example, two surfaces in rolling contact with high relative velocities create an increase in pressure at the points of contact. Lubricant viscosity is related to pressure exponentially and this large increase in pressure due to the rolling greatly increases the viscosity of the lubricant. In elastohydrodynamic lubrication, the increased viscosity creates a thin film that prevents contact between the surfaces. Elastohydrodynamic lubricants separate surfaces that are in motion (e.g., in rolling contact) at high relative speeds.

Compounds that serve well as boundary lubricants, which usually react and/or physically interact with surfaces, typically do not effectively lubricate surfaces that are in motion at high relative speeds. Conversely, elastohydroynamic lubricants provide a shear layer that separates and prevents contact between rolling surfaces. Elastohydrodynamic lubricants therefore do not serve as well at rest or at low relative speed conditions as do boundary lubricants. There are, however, systems containing contacting surfaces that require lubrication through a range of conditions, for example, from rest to high relative speeds.

DESCRIPTION OF THE INVENTION

Brief Summary of the Invention

Surprisingly, it is found that a lubricant compound that combines both an elastohydrodynamic lubricant and a boundary lubricant exhibits the opposing characteristics of each individual lubricant to provide effective lubrication over a range of conditions. Thus, the elastohydrodynamic portion of this lubricant compound prevents contact between surfaces when they are at high relative speeds, while the boundary lubricant portion chemically reacts or physically interacts with surfaces that it contacts and provides lubrication to surfaces that are at rest or at low relative speeds. The lubricating compound links an elastohydrodynamic lubricant and a boundary lubricant and provides increased performance over a range of surface lubricating conditions.

The result is surprising in that the boundary lubricant does not impede motion, while the elastohydrodynamic lubricant does not adversely affect surface reactions. It is believed that, because both lubricant functionalities are co-located on the same molecule, the lubricating molecules, even though bound, are able to slip past each other when the surfaces are in motion, yet still provide elastohydrodynamic lubrication that eases such motion.

The lubricant compound has the general formula

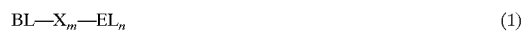

$$BL-X_m-EL_n \quad (1)$$

in which BL is a hydrocarbon boundary lubricant, X is a linking moiety, and EL is a fluorocarbon elastohydrodynamic lubricant. The hydrocarbon BL in formula 1 comprises at least one species that is reactive with the material to be lubricated. As used herein, reactive species comprise species that chemically react (e.g., bond) and/or physically interact (e.g., adsorb) with the material. The hydrocarbon BL is selected from the group consisting of alkyls, aryls, and annulenes. The hydrocarbon BL may, if desired, be substituted by one or more independently selected substituents as discussed below.

The hydrocarbon BL substitutents employed in the lubricant compound are selected because they are reactive with certain metals. Hydrocarbon BL moieties substituted with halogens are effective metal surface lubricants. Tribromophenyl, for example, is particularly well suited to lubricating surfaces comprising noble metals such as gold. Alkyl groups may similarly be employed as lubrication compound substitutents for non-noble metal surfaces. Trimethylphenyl interacts, for example, to lubricate surfaces comprising metals such as steel.

One or more fluorocarbon elastohydrodynamic lubricants (i.e., EL moieties) may be provided. Each EL moiety may be independently selected from fluorocarbons, substituted fluorocarbons, fluorocarbon ethers, perfluorocarbons, and perfluoropolyethers.

The linking moiety, X, may be one or more carbon-carbon bonds between the hydrocarbon BL and the fluorocarbon EL. The linking moiety X may also be one or more oxygen, sulfur, nitrogen, phosphorous, ester, thioester, ether, amide, phosphate ester, carbon, or ketone groups. Multiple linking groups X may bind a single BL moiety to a plurality of EL moieties. Also, one or more of the linking groups X may be multivalent such that more than one EL moiety may be bound to a single linking group X, and each such fluorocarbon EL may be independently selected.

The hydrocarbon BL and the fluorocarbon EL may be selected to provide a lubricant compound with desired lubricating properties. A lubricant compound with a low coefficient of friction is expected to reduce wear to the surfaces where the lubricant is disposed.

In use, the boundary lubricant moiety lubricates two surfaces when the surfaces are at rest or a low relative speeds with respect to each other, and the elastohydrodynamic lubricant moiety lubricates the surfaces when they are in motion at high relative speeds with respect to each other. The lubricant compound of the present invention may provide a favorably low coefficient of friction whether used alone or as an additive. Some embodiments, e.g., in extreme anti-wear applications the lubricant compound may be used alone and not as an additive to another lubricant. In other embodiments, the lubricant may be added at a percentage of weight ranging from 0.1 to 10 wt % with respect to another lubricant (e.g., a base stock). The coefficient of friction of the lubricant with additive will be comparable to that of the compound used alone.

The lubricant compound of the present invention may be tailored to be soluble in, for example, fluorocarbons or hydrocarbons. The lubricant may be used as a co-solvent for the addition of alternative additives or lubricants. Alternative additives may be used in conjunction with the instant lubricant compound. The lubricant compound may also serve as an extreme pressure additive and/or as a corrosion inhibitor. The lubricant compound may be in the form of a grease.

Detailed Description of the Preferred Embodiments
1. Lubricant Compound Structures and Corresponding Properties The hydrocarbon BL and the fluorocarbon EL shown in formula 1 are selected such that when used as a pure lubricant they are able to form a compound. However, when used as an additive, the hydrocarbon BL and the fluorocarbon EL are selected such that the lubricant compound is soluble in the base stock.

In some embodiments, the hydrocarbon BL and the fluorocarbon EL have favorable solubility when the molecular weight ratio of fluorocarbon EL to hydrocarbon BL is in the range of between about 4:1 and about 20:1. For example, in an embodiment where the hydrocarbon BL is tribromophenyl and the fluorocarbon EL is perfluoropolyalkylether lubricant where n=8, the molecular weight ratio of fluorocarbon EL to hydrocarbon BL is about 4.6:1. In an alternative embodiment, where hydrocarbon BL is phenyl and fluorocarbon EL is perfluoropolyalkylether lubricant where n=8, then the molecular weight ratio of fluorocarbon EL to hydrocarbon BL is about 19:1. Both embodiments have favorable solubility in, for example, a fluorocarbon lubricant.

The hydrocarbon BL in formula 1 comprises at least one species that is reactive or physically interactive with the material to be lubricated by the lubricant compound. The material to be lubricated may comprise, for example, metals, ceramics or both. The metals that may employ the lubricant compound include, for example, noble metals such as gold or platinum. Ceramic materials amenable to lubrication in accordance herewith include, for example, titanium carbide and silicon nitride employed alone, in combination with one another, or in combination with a metal as, for example, a coating on the metal. The hydrocarbon BL is selected from the group consisting of alkyls, aryls, and annulenes. In some embodiments the hydrocarbon BL comprises between 1 and about 30 carbon atoms. In a number of desirable embodiments the hydrocarbon BL that is selected is the annulene benzene. In other desirable embodiments, the hydrocarbon BL that is selected has two or more fused annulene rings.

The hydrocarbon BL moiety may be selected because it improves the performance of the lubricant compound under boundary lubrication conditions. The selected BL may also provide the lubricant compound with improved performance characteristics such as corrosion resistance, oxidative resistance, vapor pressure, surface tension, density, Newtonian behavior, viscosity, viscosity-temperature variation, and improved properties under extreme pressure conditions. The BL moiety may improve the above-mentioned performance characteristics of the compound when used as an additive in a base stock lubricant such as a fluorocarbon lubricant.

In some embodiments, the hydrocarbon BL is substituted. The substituents may be independently selected from halogens, nitro, cyano, amino, ester, ether, aldehydes, ketones, acetals, carboxylic acid, phenol, ketals, straight alkyl, branched alkyl, cyclic alkyl, alkyl ethers, alkyl esters and haloalkyls. The substituent alkyl groups employed may comprise between 1 and about 18 carbon atoms. In some embodiments, the alkyl substituents comprise between 1 and about 6 carbon atoms. The substituents may be reactive or, alternatively, may be physically interactive with the material to be lubricated. In one embodiment a straight alkyl comprising one carbon atom, methyl, is employed. One or more alkyl groups may substitute the hydrocarbon BL. For example, in one preferred embodiment, the hydrocarbon BL is substituted with a single methyl group. If substituted, BL may contain one or more of the foregoing substituents.

As noted previously, the hydrocarbon BL substituents are generally selected because they are reactive or physically interactive with certain materials. For example, substituting a hydrocarbon BL with halogens provides a lubrication compound that is reactive with noble metals, for example, gold. Suitable halogens include F, Cl, Br, and I. In one embodiment, the hydrocarbon BL employed in the lubrication compound is tribromophenyl, which is particularly well suited to gold surfaces.

Other BL substituents that are reactive with metals comprise straight alkyl groups. In one embodiment the hydrocarbon BL employed in the lubrication compound is trimethylphenyl which reacts to lubricate surfaces comprising non-noble metals, for example steel. Substituted aryl esters and substituted aryl amides may be employed as anti-wear agents for surfaces such as, for example, steel, bronze and aluminum.

Still other BL substituents that are reactive with metals comprise amine groups. In one embodiment, an amino-substituted hydrocarbon BL reacts with non-noble metals, for example steel or bronze. In some embodiments, the amino-substituted hydrocarbon BL comprises two or more fused annulene rings. The number of fused rings can range from 2 to about 7. Isomers of the fused ring hydrocarbon BL may be employed. For example, an amino substituted hydrocarbon BL comprising four fused rings, 6-amino-chrysene, or its isomer, 6-amino-triphenylene, may be employed and similar lubrication properties are expected from each isomer. Amine group(s) may substitute one or more of the fused rings and/or may substitute one of the fused rings of the hydrocarbon BL at multiple positions. For example, the amino-substituted hydrocarbon BL 1-amino-naphthalene and its amino-substituted isomer 2-amino-naphthalene may be employed and each isomer is expected to similarly lubricate non-noble metals such as, for example, steel.

The EL in formula 1 is a fluorocarbon that is preferably an elastohydrodynamic lubricant. One or more EL moieties may be provided (thus, in formula 1, $n \geq 1$). Each EL moiety may be independently selected from fluorocarbons, substituted fluorocarbons, fluorocarbon ethers, perfluorocarbons, and perfluoropolyethers. A fluorocarbon is a hydrocarbon in which all or some of the hydrogen atoms have been replaced by fluorine atoms. In a highly fluorinated flurocarbon, at least about half of any available hydrogen atoms have been replaced by fluorine atoms. A perfluorocarbon is a hydrocarbon in which all of the hydrogen atoms have been replaced with fluorine. In a substituted fluorocarbon, one or more of the hydrogen atoms on the hydrocarbon is substituted with a substituent other than fluorine. Other substituents may, for example, be independently selected from the other halogens. A fluorocarbon ether is a fluorocarbon in which oxygen links two fluorocarbon groups (i.e., hydrocarbon groups in which all or some of the hydrogen atoms have been replaced by fluorine atoms). A perfluoropolyether is a fluorocarbon ether in which all of the hydrogen atoms have been replaced with fluorine. Fluoroethers and perfluoroethers may have repeating structures.

The fluorocarbon EL may be selected because of its elastohydrodynamic lubricating properties. In some embodiments, for example, where the lubricant is used as an additive, the EL of the lubricating compound may be selected because it renders the lubricant compound soluble in a base stock.

The X in formula 1 is a linking moiety. Most simply, X is no more than a direct carbon-carbon bond between one or more carbons in the hydrocarbon BL and between the first fluorocarbon group in the fluorocarbon EL. However, X may also be one or more oxygen, sulfur, nitrogen, phosphorous, ester, thioester, ether, amide, phosphate ester, carbon, or ketone groups. One or more linking moieties X may be provided (thus, in formula 1, m≧1).

In the embodiments discussed above, the constituents BL, X and EL maybe covalently bonded. As shown in formula 1, a single BL moiety may be bound to a plurality of EL moieties. For example, the molecule may contain multiple linking groups X, each bound to the BL moiety and/or arranged in a repeating fashion. Alternatively or in addition, the linking group X may itself have multiple attachment sites, so that more than one EL moiety may be bound to a single linking group X. Thus, the lubricant compound may contain numerous EL moieties if both BL and X are multifunctional. Each fluorocarbon EL may be independently selected. In formula 2a, for example, the linking moiety X is a carbon atom and three independently selected fluorocarbon EL moieties are linked thereto.

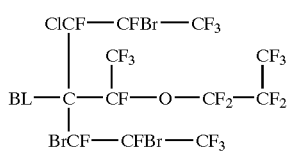
(2a)

In another embodiment, as shown in formula 2b, for example, the linking moiety X is a carbon atom and three independently selected fluorocarbon EL moieties are linked thereto.

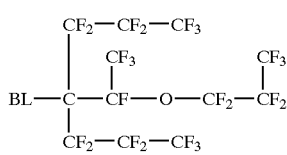
(2b)

Formula 3 illustrates an embodiment in which a single BL moiety (phenyl) is bound, at positions 1 and 4, to an ester-linking moiety that is itself bound to a perfluoromonoether EL moiety. In another embodiment, the phenyl BL moiety of formula 3 is substituted with a methyl group at any of the four open ring positions.

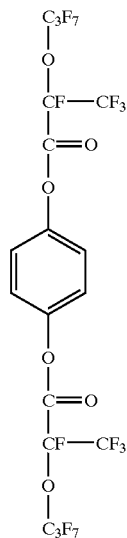
(3)

As exemplified by formula 4, the EL moieties may be independently selected (i.e., chemically different). The lubricant compound shown in formula 4 comprises a phenyl BL moiety bound, by means of ester linking groups, to a perfluoromonoether and a perfluorodiether.

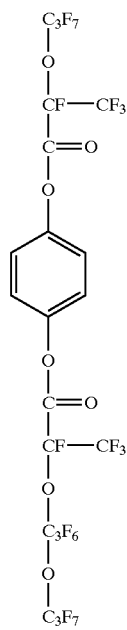
(4)

In formula 4, the BL moiety, here the phenyl group, may be substituted with one or more substituents. The substituents may be selected from the group consisting of halogens, nitro, cyano, amino, ester, ether, aldehydes, ketones, acetals, alkyls, carboxylic acid, phenol and ketals. In one embodiment, the BL moiety (phenyl) of formula 4 is substituted with a methyl group at any of the four open ring positions.

Formula 5 shows a lubricant compound in accordance with the invention where the BL moiety is multifunctional (i.e., bound to more than one linking group X) and the EL moieties may be independently selected (i.e., chemically different). The lubricant compound shown in formula 5 comprises a phenyl BL moiety bound, by means of a amide linking group to a perfluoromonoether and the BL moiety is also bound by means of an ester to a perfluorodiether.

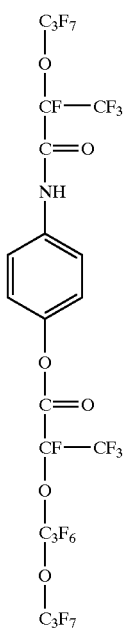

(5)

Formula 6 shows a lubricant compound in accordance with the invention in which the BL moiety is multifunctional (i.e., bound to more than one linking group X) and one of the linking groups is itself multivalent, so that BL is bound to four EL moieties. In particular, the linking moieties X are carbon and oxygen. The oxygen atom links BL to a chlorine-substituted fluorocarbon. The carbon atom is bound to a bromine-substituted fluorocarbon and two perfluoropolyethers, i.e. a perfluoromonoether and a perfluorodiether.

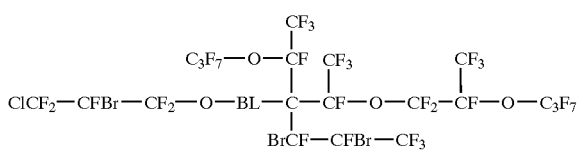

(6)

Formula(s) 7a and 7b show lubricant compounds in accordance with the invention where the BL moiety comprises four fused annulene rings and where isomers of the BL moiety have similar lubricating properties. The lubricant compound shown in formula 7a comprises a 6-amino-triphenylene BL moiety bound, by means of an amide linking group, to a perfluromonoether EL moiety. The lubricant compound shown in formula 7b comprises the BL moiety isomer, 6-amino-chrysene, bound by means of an amide linking group to a perfluromonoether EL moiety.

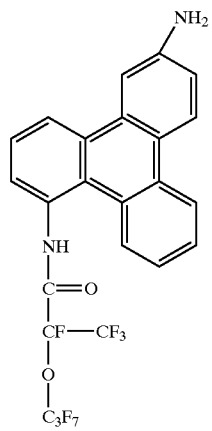

(7a)

(7b)

Formula 7c shows a lubricant in accordance with the invention in which an amino-substituted isomer of the BL moiety shown in Formula 7b, namely, 5-amino-chrysene is bound, by means of an amide linking group, to a perfluromonoether EL moiety. The lubricant compounds shown in Formula(s) 7a, 7b and 7c are expected to have similar lubrication properties.

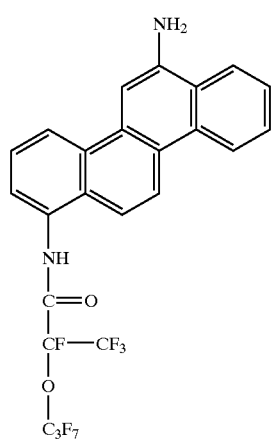

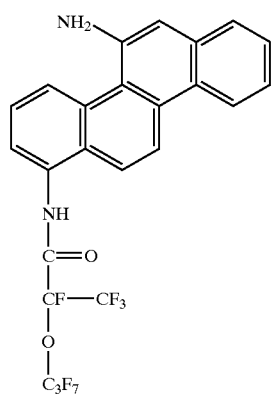

(7c)

In general, the hydrocarbon BL and the fluorocarbon EL may be selected to provide desired lubricating properties. The effectiveness of the lubricating compound at preventing wear may be determined by methods including measurement of lubricant coefficient of friction. In use, a lubricant comprising a low coefficient of friction is expected to reduce wear to the surfaces where the lubricant is disposed. The lubricant coefficient of friction may be determined as it relates to different surfaces. The surfaces may comprise, for example, the same or different metals.

The hydrocarbon BL and the fluorocarbon EL employed to make the lubricating compound of the invention are preferably selected such that, if the compound is used as an additive, it is soluble in the base stock being employed. Thickeners may be added to the lubricating compound of the invention to form grease. Suitable thickeners may include silica gel and high molecular weight polymers such as, for example, polyisobutylene. Such grease may retain the favorable properties of the lubricant compound. In addition, the structure of the hydrocarbon BL and the fluorocarbon EL present in a lubricating compound may also be selected according to the expected (i.e., corresponding) lubricating properties.

A lubricant compound with a low coefficient of friction is expected to reduce wear to the surfaces where the lubricant is disposed. The lubricating properties for a compound may be optimized by tailoring the steric hindrance of the hydrocarbon BL to the reactivity of the surface where the lubricant is disposed. Furthermore, the substituents on the hydrocarbon BL may be selected for the individual metal surface, the temperature, and the range of relative speeds, if any, over which the surfaces will be in motion.

Otherwise identical lubricating compounds with substituents having different steric hindrances will exhibit different coefficients of friction. For example, where the surface comprises a noble metal and the hydrocarbon BL is an aromatic ring that is halogen substituted, a lubricating compound with higher steric hindrance tends to exhibit a lower coefficient of friction. The increase in steric hindrance on the aromatic ring hydrocarbon results in reduced bond strength. This reduced hydrocarbon BL bond strength is believed to correlate with the reduced lubricant compound coefficient of friction. It is found, however, that where noble metal surfaces are being lubricated, the aromatic hydrocarbon ring electron density does not have a strong impact on lubricant coefficient of friction.

Similarly, where the surfaces comprise a noble metal, given two lubricating compounds having an identical linking moiety X, an identical fluorocarbon EL, and a hydrocarbon BL that is an aryl group substituted with one or more halogens, the coefficient of friction value of each lubricant compound will vary according to the halogen substituent. For example, tribromo-substituted lubricant compounds will provide a lower coefficient of friction than an otherwise identical trichloro-substituted compound with respect to surfaces comprising gold. Thus, generally, the higher the atomic number of the substituted halogen on the hydrocarbon BL, the lower will be the expected coefficient of friction in otherwise identical lubricating compounds. In one embodiment, a tribromo substituted hydrocarbon BL is employed to lubricate a surface comprising the noble metal gold where the surfaces are at the temperature 125° F. and the surfaces move, with respect to one another, at the speed 10 RPM.

Similar effects are observed when substitutions are made on the EL moiety. For example, given two halogen-substituted lubricating compounds having identical linking moieties X linked to a hydrocarbon BL, the coefficient of friction value of each lubricant compound is determined by the halogen substituent. Thus, in otherwise identical lubricating compounds a bromine-substituted fluorocarbon will provide a lower coefficient of friction than a chlorine-substituted fluorocarbon EL when employed on surfaces comprising gold. In general, the higher the atomic number of the fluorocarbon EL substituent, the lower will be the expected coefficient of friction in otherwise identical lubricating compounds. It is also found, however, that with otherwise identical lubricating compounds, the fluorocarbon EL side chain length does not have a corresponding impact on the expected coefficient of friction of the lubricating compound.

Thus, the lubricating compound combine a hydrocarbon BL and one or more fluorocarbon EL moieties that are each substituted to effect a desired lubricant compound coefficient of friction, thereby optimizing lubrication for particular surfaces.

2. Methods of Lubricating Employing the Lubricant Compound

A method of lubricating two surfaces may employ the lubricant compound of the present invention, where a linking moiety X links a fluorocarbon elastohydrodynamic-lubricant moiety and a boundary-lubricant moiety. The lubricant compound may be used alone or as an additive to another lubricant. The lubricant compound or composition is applied to the surfaces, lubricating them over conditions ranging from complete rest to low-speed relative motion to high-speed relative motion. When surfaces are at rest or at a low relative speed, the boundary lubricant provides a protective stationary film that discourages contact between the first surface and the second surface. This occurs through controlled chemical reaction and physical interaction between the boundary-lubricant moiety and one or both surfaces. The elastohydrodynamic-lubricant moiety provides lubrication when the first and second surfaces are in motion at high relative speeds, creating a thin film that separates the surfaces and prevents the surfaces from contacting one another. The elastohydrodynamic-lubricant moiety enables the two surfaces that are in close contact at high pressures to avoid interaction even at surface asperities (e.g., surface roughness or surface imperfections).

The lubricant compound of the present invention may provide a favorably low coefficient of friction whether used alone or as an additive to another lubricant. In some embodiments, the lubricating compound is added to another lubricant at a percentage of weight ranging from about 0.1 to 100 wt %. In another embodiment the lubricating compound is added to another lubricant at a percentage of weight ranging from about 0.1 to 70 wt %. In yet another embodiment, the lubricating compound is added to another lubricant at a percentage of weight ranging from about 0.1 to 30 wt %. In still another embodiment, the lubricating compound is added to another lubricant at a percentage of weight ranging from about 0.1 to 10 wt %. In yet another embodiment, the lubricating compound is added to another lubricant at a percentage of weight ranging from about 0.1 to 1 wt % A lubricating compound well suited to use as an additive is shown in formula 8.

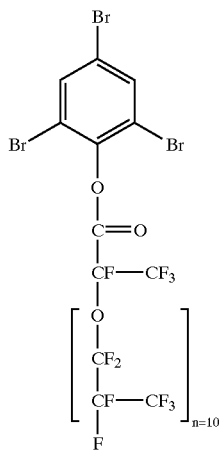

(8)

In formula 8, BL is tibromophenyl, X is an ester linkage, and EL is a perfluoropolyether having a repeating structure. In some embodiments, the repeating structure may range between about n=10 and about n=60. As the lubricant compound of formula 8 has a tribromo substitution, it will provide a favorably low coefficient of friction when introduced to surfaces comprising gold.

When the lubricant compound of formula 8 is added at a level of 0.1 to 1 wt % to the KRYTOX 143AZ fluorocarbon lubricant (which has an average molecular weight of 1850 g/mole) supplied by E. I. du Pont de Nemours and Company, Wilmington Del., the added lubricant compound will lower the lubricant coefficient of friction. Indeed, the KRYTOX 143AZ with the additive will have a coefficient of friction comparable to that of the additive used alone.

Generally, perfluorotributylamine is not considered a particularly good lubricant. Perfluorotributylamine does not separate surfaces that are moving at high relative speeds as elastohydrodynamic lubricants do and because it is relatively inert it does not react or physically interact with surfaces, as do boundary lubricants. Adding the lubricant compound of formula 8 at a level ranging from 0.1 to 1 wt % by weight to perfluorotributylamine results in a coefficient of friction similar to that obtained when the lubricant of formula 8 is used alone.

Using the lubricant compound of the instant invention as an additive to other lubricants improves the coefficient of friction of existing lubricants. By employing the lubricant compound at relatively low levels, the cost of this improvement is minimized. Furthermore, use of the lubricant compound as an additive enables continued use of lubricants that provide other beneficial properties while improving the alternative lubricant coefficient of friction.

3. Experimental Results

Experiment Number 1

A number of lubricant compounds were evaluated. The experimental lubricant compounds that were tested had an average molecular weight consistent with an EL moiety where n=7, i.e. about 1366 g/mole. A four-ball wear test employing balls and test equipment fabricated from 52100 steel was conducted for one hour at a temperature of 70° C. with the equipment speed set at 800 RPM. During the four-ball wear test, three of the balls were arranged so that each ball touches the other two balls, forming a shape about the exterior of the three balls like a triangle. The fourth ball was placed on the top of the three balls. Thereafter, a 4 kilogram load was placed on the fourth ball for the duration of the test. Profilometry traces were employed to measure wear depth in microinch units. The wear depth measurement measures the surface finish on the ball by calculating the difference between the peak and the valley of the wear scar on the most worn of the three lower balls after the test.

Table 1 presents the wear depth measurement results where the lubricant compounds of Experiment Number 1 were added at 100% by weight.

TABLE 1

| Compound Number | Lubricant Compound | Wear Depth (microinches) | % Wear Relative to Compound Number 1 |
|---|---|---|---|
| 1 | phenyl–O–C(=O)–CF(CF$_3$)–[O–CF$_2$–CF(CF$_3$)]$_{n=7}$–F | 60.03 | 100% |
| 2 | C$_6$F$_5$–O–C(=O)–CF(CF$_3$)–[O–CF$_2$–CF(CF$_3$)]$_{n=7}$–F | 140.46 | 234% |

TABLE 1-continued

| Compound Number | Lubricant Compound | Wear Depth (microinches) | % Wear Relative to Compound Number 1 |
|---|---|---|---|
| 3 | 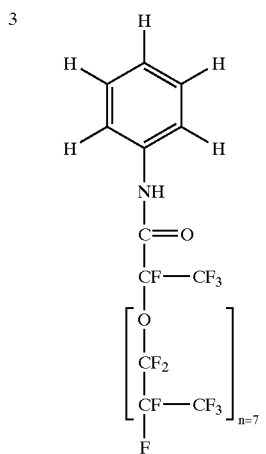 | 109.77 | 183% |
| 4 | 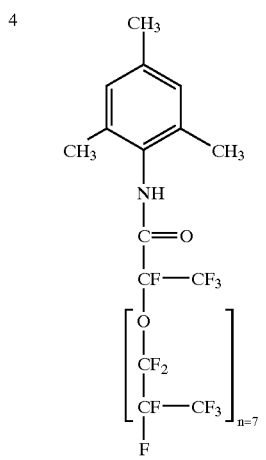 | 10.66 | 18% |
| 5 | 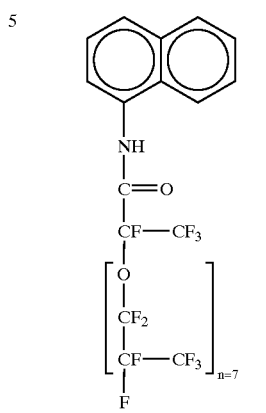 | 5.44 | 9% |
| 6 | ![compound 6] | 9.6 | 16% |
| 7 | ![compound 7] | None Visible | About 0% |

Table 2 presents the wear depth measurement results where lubricant compound number 4 from Table 1 was added into the lubricant compound number 1 from Table 1 over a weight percent range as indicated.

TABLE 2

| % of Compound Number 1 (% by Weight) | % of Compound Number 4 (% by Weight) | Wear Depth (microinches) | % Wear Relative to Compound Number 1 |
|---|---|---|---|
| 100% | 0% | 60 | 100% |
| 98% | 2% | 54 | 90% |
| 95% | 5% | 47 | 78% |
| 90% | 10% | 30 | 50% |
| 0 | 100% | 5–10 | 8%–17% |

Experiment Number 2

Two lubricant compounds were evaluated. The experimental lubricant compounds that were tested had an average molecular weight consistent with an EL moiety where n=10, i.e. about 1900 g/mole. A four-ball wear test as described in connection with Experiment Number 1 was conducted on the two samples. The test equipment was fabricated from 52100 steel, a 4 kilogram load was placed on the fourth ball for the duration of the test, the test was conducted for one hour at a temperature of 70° C. and the equipment speed set was at 800 RPM. As described above the fourth ball was placed on the top of the three balls, which were arranged in a triangular configuration. Thereafter, profilometry traces were employed to measure wear depth in microinch units by calculating the difference between the peak and the valley of the wear scar on the most worn of the three lower balls.

Table 3 presents the wear depth measurement results where the lubricant compounds of Experiment Number 2 were added at 100% by weight.

TABLE 3

| Compound Number | Lubricant Compound | Wear Depth (microinches) | % Wear Relative to Compound Number 1 |
|---|---|---|---|
| 8 | 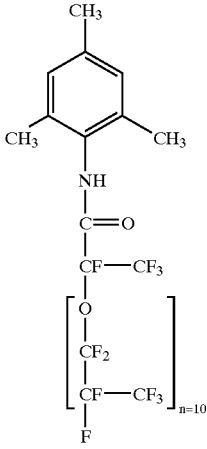 | None Visible | 0% |
| 9 | 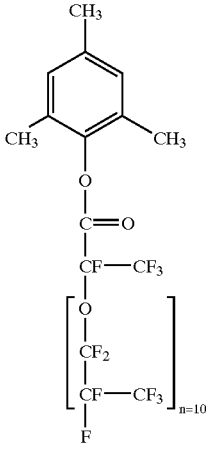 | 16.81 | 28% |

As illustrated by the experimental results presented in Table 3, amide lubricant compounds appear to be more effective anti-wear lubricants than ester lubricant compounds. Amide lubricant compounds are also expected to be more effective thermally and hydrolytically than the comparable ester lubricant compound. The amount of wear appears to decrease as the concentration of the amide within the lubricant compound is increased.

Although the present invention has been described with reference to specific details, it is not intended that such details should be regarded as limitations upon the scope of the invention, except as and to the extent that they are included in the accompanying claims.

What is claimed is:

1. A lubricant compound comprising the formula:

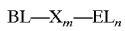

wherein:
BL is a hydrocarbon that is a boundary lubricant;
EL is a fluorocarbon that is an elastohydrodynamic lubricant, wherein $n \geq 1$; and
X is a linking moiety selected from the group consisting of sulfur, nitrogen, phosphorous, thioesters, amides, phosphate ester, and ketones, wherein $m \geq 1$.

2. The lubricant compound of claim 1, wherein BL comprises at least one species interactive with a material to be lubricated.

3. The lubricant compound of claim 2, wherein BL is selected from the group consisting of alkyls, aryls, and annulenes.

4. The lubricant compound of claim 3, wherein BL comprises two or more fused annulenes.

5. The lubricant compound of claim 3, wherein BL comprises between 1 and about 30 carbon atoms.

6. The lubricant compound of claim 3, wherein BL comprises at least one substituent interactive with the material to be lubricated.

7. The lubricant compound of claim 6, wherein the at least one substituent is selected from the group consisting of halogens, nitro, cyano, amino, ester, ether, aldehydes, ketones, acetals, carboxylic acid, phenol and ketals.

8. The lubricant compound of claim 6, wherein the at least one substituent is selected from the group consisting of straight alkyls, branched alkyls, cyclic alkyls, alkyl ethers, alkyl esters and haloalkyls.

9. The lubricant compound of claim 8, wherein the alkyls comprise between 1 and about 6 carbon atoms.

10. The lubricant compound of claim 1, wherein each EL is independently selected from the group consisting of fluorocarbons, substituted fluorocarbons, fluorocarbon ethers, perfluorocarbons, and perfluoropolyethers.

11. The lubricant compound of claim 10, wherein at least one EL is a substituted fluorocarbon substituted with at least one independently selected halogen.

12. The lubricant compound of claim 10, wherein at least one EL is a highly fluorinated fluorocarbon.

13. A lubricant compound comprising the formula:

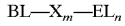

wherein:
BL is a tribromophenyl;
EL is a fluorocarbon that is an elastohydrodynamic lubricant, wherein $n \geq 1$; and
X is a linking moiety, wherein $m \geq 1$.

14. A lubricant compound comprising the formula:

wherein:
BL is a trimethylphenyl;
EL is a fluorocarbon that is an elastohydrodynamic lubricant, wherein $n \geq 1$; and
X is a linking moiety, wherein $m \geq 1$.

15. A lubricant compound comprising the formula:

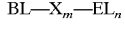

wherein:

BL is a 6-amino-chrysene or hydrocarbon isomers thereof;

EL is a fluorocarbon that is an elastohydrodynamic lubricant, wherein n≧1; and

X is a linking moiety, wherein m≧1.

16. A lubricant compound comprising the formula:

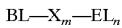

wherein:

BL is a 6-amino-chrysene or amino substituent isomers thereof;

EL is a fluorocarbon that is an elastohydrodynamic lubricant, wherein n≧1; and

X is a linking moiety, wherein m≧1.

17. The lubricant compound of claim 10, wherein EL is the perfluoropolyether:

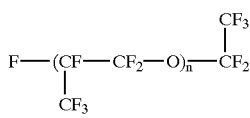

and wherein n≧1.

18. A lubricant compound comprising the formula:

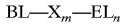

wherein:

BL is a hydrocarbon that is a boundary lubricant;

EL is a fluorocarbon that is an elastohydrodynamic lubricant, wherein n≧1; and

X is an amide group, wherein m≧1.

19. The lubricant compound of claim 1, wherein the lubricant compound is an additive added to a base lubricant.

20. The lubricant compound of claim 19, wherein the lubricant compound is added at between about 0.1 to about 10 weight percent to the base lubricant.

21. A method of lubricating first and second surfaces, the method comprising the steps of:

providing a lubricant compound comprising (i) a hydrocarbon boundary-lubricant moiety, (ii) a fluorocarbon elastohydrodynamic-lubricant moiety and (iii) a linking moiety linking the boundary-lubricant moiety to the elastohydrodynamic-lubricant moiety, wherein the linking moiety comprises at least one of sulfur, nitrogen, phosphorous, thioesters, amides, phosphate ester, and ketones; and introducing the lubricant compound to the surfaces, the boundary-lubricant moiety lubricating the first and second surfaces when the surfaces are at rest or in motion at low relative speeds with respect to each other and the elastohydrodynamic-lubricant moiety lubricating the first and second surfaces when the surfaces are in motion at high relative speeds with respect to each other.

22. The method of claim 21, wherein the hydrocarbon boundary-lubricant moiety is selected from the group consisting of alkyls, aryls, and annulenes.

23. The method of claim 22, wherein the hydrocarbon boundary-lubricant moiety comprises two or more fused annulenes.

24. The method of claim 21, wherein the hydrocarbon boundary-lubricant moiety comprises between 1 and about 30 carbon atoms.

25. The method of claim 21, wherein the hydrocarbon boundary-lubricant moiety is substituted.

26. A method of lubricating first and second surfaces, the method comprising the steps of:

providing a lubricant compound comprising (i) a hydrocarbon boundary-lubricant moiety substituted with at least one substituent selected from the group of halogens, nitro, cyano, amino, ester, ether, aldehydes, ketones, acetals, carboxylic acid, phenol and ketals, (ii) a fluorocarbon elastohydrodynamic-lubricant moiety and (iii) a linking moiety linking the boundary-lubricant moiety to the elastohydrodynamic-lubricant moiety; and introducing the lubricant compound to the surfaces, the boundary-lubricant moiety lubricating the first and second surfaces when the surfaces are at rest or in motion at low relative speeds with respect to each other and the elastohydrodynamic-lubricant moiety lubricating the first and second surfaces when the surfaces are in motion at high relative speeds with respect to each other.

27. The method of claim 25, wherein the at least one substituent is selected from the group of straight alkyl, branched alkyl, cyclic alkyl, alkyl ethers, alkyl esters, and haloalkyls.

28. The method of claim 27, wherein the alkyls comprise between 1 and about 6 carbon atoms.

29. A method of lubricating first and second surfaces, the method comprising the steps of:

providing a lubricant additive comprising (i) a hydrocarbon boundary-lubricant moiety, (ii) a fluorocarbon elastohydrodynamic-lubricant moiety and (iii) a linking moiety linking the boundary-lubricant moiety to the elastohydrodynamic-lubricant moiety, wherein the linking moiety comprises at least one of sulfur, nitrogen, phosphorous, thioesters, amides, phosphate ester, and ketones;

adding the lubricant additive to a base lubricant;

introducing the base lubricant with lubricant additive to the surfaces, the boundary-lubricant moiety lubricating the first and second surfaces when the surfaces are at rest or in motion at low relative speeds with respect to each other and the elastohydrodynamic-lubricant moiety lubricating the first and second surfaces when the surfaces are in motion at high relative speeds with respect to each other.

30. The method of claim 29, wherein the lubricant additive is added at between about 0.1 to about 10 weight percent to the base lubricant.

31. The method of claim 29, wherein the hydrocarbon boundary-lubricant moiety is selected from the group consisting of alkyls, aryls, and annulenes.

32. The method of claim 31, wherein the hydrocarbon boundary-lubricant moiety comprises two or more fused annulenes.

33. The method of claim 29, wherein the hydrocarbon boundary-lubricant moiety comprises between 1 and about 30 carbon atoms.

34. The method of claim 29, wherein the hydrocarbon boundary-lubricant moiety is substituted.

35. A method of lubricating first and second surfaces, the method comprising the steps of:

providing a lubricant additive comprising (i) a hydrocarbon boundary-lubricant moiety substituted with at least one substituent selected from the group of halogens, nitro, cyano, amino, ester, ether, aldehydes, ketones, acetals, carboxylic acid, phenol and ketals, (ii) a fluorocarbon elastohydrodynamic-lubricant moiety and (iii) a linking moiety linking the boundary-lubricant moiety to the elastohydrodynamic-lubricant moiety;

adding the lubricant additive to a base lubricant;

introducing the base lubricant with lubricant additive to the surfaces, the boundary-lubricant moiety lubricating the first and second surfaces when the surfaces are at rest or in motion at low relative speeds with respect to each other and the elastohydrodynamic-lubricant moiety lubricating the first and second surfaces when the surfaces are in motion at high relative speeds with respect to each other.

36. The method of claim 34, wherein the at least one substituent is selected from the group of straight alkyl, branched alkyl, cyclic alkyl, alkyl ethers, alkyl esters, and haloalkyls.

37. The method of claim 36, wherein the alkyls comprise between 1 and about 6 carbon atoms.

38. The lubricant compound of claim 1, wherein BL is 1-amino-naphthalene or amino substituent isomers thereof.

39. The lubricant compound of claim 21, wherein BL is 1-amino-naphthalene or amino substituent isomers thereof.

40. The lubricant compound of claim 29, wherein BL is 1-amino-naphthalene or amino substituent isomers thereof.

* * * * *